(12) United States Patent
Haszler et al.

(10) Patent No.: US 6,234,020 B1
(45) Date of Patent: May 22, 2001

(54) METHOD FOR RESIDUAL STRESS MEASURING

(75) Inventors: Alfred Johann Peter Haszler, Vallendar (DE); Hormoz Ghaziary, Los Gatos, CA (US)

(73) Assignee: Hoogovens Aluminum Walzprodukte, Koblenz (DE)

( * ) Notice: Subject to any disclaimer, the term of this patent is extended or adjusted under 35 U.S.C. 154(b) by 0 days.

(21) Appl. No.: 09/402,901

(22) PCT Filed: May 15, 1998

(86) PCT No.: PCT/EP98/03003

§ 371 Date: Jan. 13, 2000

§ 102(e) Date: Jan. 13, 2000

(87) PCT Pub. No.: WO98/52032

PCT Pub. Date: Nov. 19, 1998

(30) Foreign Application Priority Data

May 15, 1997 (EP) .................................................. 97201471

(51) Int. Cl.[7] .................................................. G01H 11/08
(52) U.S. Cl. ................................ 73/579; 73/599; 73/600; 73/602
(58) Field of Search ............................ 73/579, 599, 600, 73/602

(56) References Cited

U.S. PATENT DOCUMENTS

| | | | |
|---|---|---|---|
| 3,991,607 | 11/1976 | Niklas | 73/602 |
| 4,566,330 * | 1/1986 | Fujii et al. | 73/599 |
| 5,305,239 * | 4/1994 | Kinra | 73/602 |
| 5,474,070 | 12/1995 | Ophir et al. | 600/437 |

FOREIGN PATENT DOCUMENTS

| | | |
|---|---|---|
| 0395475 | 10/1990 | (EP) . |
| 0456028 | 11/1991 | (EP) . |

* cited by examiner

*Primary Examiner*—Hezron Williams
*Assistant Examiner*—Jacques Saint-Surin
(74) *Attorney, Agent, or Firm*—Stevens, Davis, Miller & Mosher, LL

(57) ABSTRACT

Method for measuring residual stress in a metallic specimen wherein, by means of an ultrasound transducer an ultrasound entry wave having a ground frequency is introduced into a surface of the metallic specimen, the ultrasound entry wave is measured by means of an entry wave detector and the succeeding ultrasound exit wave is measured by means of a exit wave detector and the measured values of the ultrasound entry and exit wave are used to determine residual stress, characterized in that, for a selected entry gate time the value of the entry convolution integral of the measured ultrasound entry wave and a periodic wave of the ground frequency is calculated and during a selected exit gate time the value of the exit convolution integral of the measured ultrasound exit wave and a periodic wave of the ground frequency is calculated and the residual stress is determined using the calculated values of the entry convolution integral and the exit convolution integral.

8 Claims, 3 Drawing Sheets

FIG. 7 AREA SCAN OF THE RESIDUAL STRESS FACTOR OBTAINED BY APPLYING THE PROCEDURE FOR EACH SCAN INCREMENT

METHOD FOR RESIDUAL STRESS MEASURING

The invention relates to a method for measuring residual stress in a metallic specimen wherein, by means of an ultrasound transducer an ultrasound entry wave having a ground frequency is introduced into a surface of the metallic specimen, the ultrasound entry wave is measured by means of an entry wave detector and the succeeding ultrasound exit wave is measured by means of a exit wave detector and the measured values of the ultrasound entry and exit wave are used to determine residual stress.

This method is in particular applicable and suitable for determining and mapping the values and distribution of residual stress in an entire aluminium plate, in a non-destructive fashion, using ultrasound scanning techniques. Although the invention will in the following be explained with respect to this application, the invention is not restricted thereto, but may also be applied to measure other mechanical or microstructural parameters such as grain size distribution or texture.

Rolled aluminium plates are routinely used for the manu-facturing of complex machined parts. The use of rolled aluminium plates is of particular interest in aircraft and aerospace industries due to fairly uniform and predictable internal structure and mechanical properties as compared with those of forged or cast aluminium primary products. The manufacturing of aluminium plates is a multi-step process and includes casting of ingots, hot rolling the ingots to the desired thickness, normally up to 275 mm, several steps of heat treatment, and the application of mechanical work such as stretching or cold compression. During the course of the manufacturing process, stress is formed in the plate which is removed for the most part by heat treatment and the application of mechanical work. Some residual stresses might, however, remain in the plate. Depending on the magnitude of residual stress, the integrity of the plate may be jeopardized. For example, during the process of machining complex parts out of aluminium plates, residual stresses are relieved after every step of the machining operation. This results in some distortion each time. This may sometimes render the machined part completely unsuit-able for the application for which it is intended. For many parts machined from rolled aluminium plates, for example those used in aircraft construction, the machining operation is a complex and prolonged process. Distortions due to residual stress in plates are often discovered when a con-siderable amount of material and production time is already consumed. It is, therefore, of great importance to both, producer and end user of aluminium plates to ascertain that the residual stress in these plates are at their minimum. This is only possible by using a non-destructive method which enables the measurement of residual stresses in an entire plate, and is suitable for being used online.

There are a number of test methods which are currently used by plate manufacturers to obtain an indication of the magnitude of residual stress in each individual plate. In one such test method, known under specification number BMS 7-323 a specimen is removed from a specified area of the plate and clamped in a fixed position. Several layers of specified thickness are removed from the specimen by machining and at each step, the magnitude of deflection is measured by a deflection gage. One deficiency of this method is that it is a destructive test. The specimen can only be taken from the areas near the end of a plate. Furthermore, cutting the specimen will result in releasing some of the stress. As a result, the test does not represent an entire plate with any accuracy.

Another method often used is the "Standard Test Method for Determining Residual stresses by the Hole-Drilling Strain-Gage Method" prescribed by ASTM E 837-92. In this method three strain gages are placed over the area of interest on the plate and a hole is drilled in the geometric centre of the strain gage rosette. The relieved strains are measured with a strain recording instrument and the results are related to the level of residual stress in the area of interest. One disadvantage of this method is its semi-destructive nature; it leaves the plate with shallow holes at the tested areas which may affect the use of the plate for further processing. Furthermore, in order to assess the level of residual stresses in the entire plate, numerous holes must be drilled; this process is not only time consuming, but affects the future use of the plate as well.

There are a number of non-destructive test methods which are known to have been tried as a tool to evaluate residual stresses and yet none of them were found suitable for routine operation. One example is the use of x-ray diffraction techniques as described in ASTM E 915-90. Another example is the use of photo elastic methods which was originally designed for the determination of residual stress in a transparent specimen, using polarizing micro-scope and optical retardation compensation procedures as described in ASTM C 978-87. Both of the above methods require elaborate laboratory work and the test results have been inconclusive.

Also other parameters of a metallic specimen, in particu-lar parameters relating to the bulk of the specimen such as grain size distribution and texture, are commonly deter-mined by taking a sample of the specimen at the spot of interest and performing an off-line test to establish the value of the parameter of interest. Just like described above in relation to residual stress measurement, also the determina-tion of these parameters suffer from the drawback that the determination is offline, destructive, time consuming and restricted to relative small areas.

EP-A-0 456 028 discloses an inspection apparatus uti-lizing a pulse compression which apparatus comprises a signal generator, a transmission/reception probe; first and second correlators and an adder. The signal generator gen-erates a composite transmission signal consisting of signals Sap(t), Sbp(t) and Sbq(t) respectively based on a basic unit signal ga(t) and a sequence {p}, the signal ga(t) and a sequence {q}, a basic unit signal gb(t) and the sequence {p}, and the signal gb(t) and the sequence {q}, to the probe to transmit the composite transmission signal to a target. The first correlator performs a correlation operation of echo signals Rap(t), Raq(t), Rbp(t) and Rbq(t) corresponding to the signal Sap(t), Saq(t), Sbp(t) and Sbq(t) by utilizing reference signals Ua(t) and Ub(t) based on the sequences to provide results Caap(t), Caaq(t), Cbbp(t) and Cbbq(t). The second correlator performs a correlation operation of the results Caap(t), Caaq(t), Cbbp(t) and Cbbq(t) by utilizing the sequences {p} and {q} to provide compresses pulses Caapp (t), Caaqq(t), Cbbpp(t) and Cbbqq(t). These pulses are summed up at the adder to provide a composite compressed pulse C having the large amplitude main lobe and small amplitude side lobes. An object of the disclosed invention is to provide an inspection apparatus which is capable of obtaining a compressed pulse having side lobes with a low level, preferably zero, in addition to being inexpensive and capable of attaining a high operational speed.

U.S. Pat. No. 5,474,070 discloses an ultrasonic pulse-echo method and apparatus that has particular application in making precision measurements of compressibility in any backscattering material, in particular organic tissue. The method employs a standard transducer or transducer containing device which is translated transaxially, thereby compressing or displacing a proximal region of a target body in small known increments. At each increment, a pulse is emitted and an echo sequence (A-line) is detected from regions within the target along the sonic travel path or beam of the transducer.

Resulting time shifts in echo segments corresponding to features in the target, corrected for regions of varying sonic speed along the sonic path, provide relative and quantitative information concerning the strain caused by the compressions. The stress imparted by the transducer and containing device is also determined, corrected for depth along the sonic path. The appropriate values for stress are divided into the respective values for strain along each path to yield an elastogram, or array of compressibility values, of the target.

The object of the present invention is to provide a method for on-line non-destructive measurement of parameters such as grain size distribution, texture and in particular of residual stresses in an entire metallic specimen such as an aluminium specimen, more in particular in an entire rolled aluminium plate. This object is attained by a method that is characterized in that for a selected entry gate time $\tau_n$, the value of $$\int_o^{\tau_n} w_n(t) p_n(x-t) dt$$

wherein x is a constant, this integral also referred to as the entry convolution integral, of the measured ultrasound entry wave $w_n(t)$ and a periodic wave $p_n(t)$ of the ground frequency $f_g$ is calculated and during a selected exit gate time $\tau_x$ the value of $$\int_o^{\tau_x} w_x(t) q_x(y-t) dt$$

wherein y is a constant, this integral also referred to as the exit convolution integral, of the measured ultrasound exit wave $w_x(t)$ and a periodic wave $q_x(t)$ of the ground frequency $f_g$ is calculated and the residual stress is determined using the calculated values of the entry convolution integral and the exit convolution integral.

For the sake of this description the convolution integral for both the entry wave and the exit wave is defined as $$\int_o^{\tau} w(t) p(x-t) dt$$

wherein $\tau$ is the gate time, w(t) is the measured ultrasound wave and p(t) is the periodic wave of the ground frequency. Preferably, for reasons of simplicity without harming accuracy or sensitivity, the value of the integral is calculated for x=0. The defined convolution integral is also referred to as the cross-correlation between w(t) and p(t). The value of the convolution integral can be calculated using analog electronic computing circuiting or analog computers. However a faster and more versatile way of calculation the value of the convolution integral is to use a digital computer. In that case the output of the detectors is sampled at regular intervals and the periodic wave is defined by way of an array comprising the value of the periodic wave at the same interval at which the ultrasonic wave is sampled. By multiplying the sampled value with the defined value of the array of corresponding moments within the gate time and summing the results of the multiplication, the value of the convolution integral can be determined. For enhancing the sensitivity of the method of the invention, at least the exit gate time has a length unequal to an integral multiple of the period of the ground frequency.

The invention is based on the new and inventive insight that the value of the convolution integral calculated in accordance with the proposed method is very sensitive to variations in the phase-angle of the component of the exit wave with a wave length corresponding to the wave length of the periodic wave of the ground frequency.

Expressed in physical terms, the method according to the invention is based on the measurement of ultrasound attenuation for longitudinal waves of a selected frequency, influenced by variations of ultrasound velocity at a selected frequency range across the thickness of the specimen under test and combining them in a mathematical function whose value is very sensitive to the parameter to be measured, such as residual stress.

The measurement method according to the invention is particularly suitable to be carried out continuously. In case of residual stress measurement on an entire plate, the entire plate can be scanned using an immersion technique while the measurement of a "residual stress factor" is performed on-line. The test result may be presented in the form of a C-scan in which the variations and distribution of residual stress is demonstrated.

The general procedure for the measurement of attenuation is to place the specimen in the path of ultrasound waves generated by an ultrasound transducer. At least two signals are needed to calculate the attenuation; a reference signal and a succeeding exit transmitted or echo signal both of which unsaturated. Where in this description reference is made to entry ultrasound wave, this should be understood as comprising any reference signal or wave as commonly used in ultrasound measurements. When contact measurement is used, the reference signal could be an early echo. For specimens such as plate sections, it is more practical to use an immersion technique where both the transducer and the specimen are immersed in a liquid couplant; usually water. Any two echoes may be used for reference (entry wave) and return (exit wave) signals. For thick sections the entry surface signal is usually used for reference signal and the first echo reflected from the back surface as the return echo. This is because for thick sections, the multiple back reflections are too weak for accurate measurement.

The above method according to the invention may be used to calculate the attenuation coefficient as a basis for the residual stress measurement at a single frequency. In practice ultrasound transducers do not operate with a single frequency; rather they have a usable frequency range.

The proposed method entails the additional advantage that the processing of the entry wave and the exit wave by convolution brings about a filtering of the ground frequency and a rejection of spurious signals.

An improvement in sensitivity of the method of the invention is obtained with an embodiment that is characterized in that the value of the convolution integral for both the entry wave and the exit wave is calculated for two symmetrical $\pi/2$ shifted periodic waves and the residual stress is calculated from the ratio of the square root of the sum of the squares of the calculated values of the exit convolution integrals and the entry convolution integrals respectively.

In this embodiment optimum use is made of the information content in the entry wave and the succeeding exit wave. The resultant ratio is very sensitive to the phase of the component of the exit wave with a frequency equal to the ground frequency. The resultant ratio may be considered as a first order approximation of the ratio of the power of the exit wave and the entry wave.

An embodiment of the method of the invention that is easy to carry out, both with digital computers and with electronic analog hardware is characterized in that the periodic waves $p_n(t)$ and $q_x(t)$ are sine-waves.

Preferably, for processing the entry wave, the amplitude of the periodic wave is equal to the amplitude of the entry wave and preferably for processing the exit wave, the amplitude of the periodic wave is equal to the amplitude of the exit wave.

The periodic wave such as a sine wave, and when desired also a cosine wave can be defined as an array in a digital computer or can by known electronic circuits be generated with high accuracy of the selected and desired ground frequency. The calculations are preferably carried out using a digital computer.

A further embodiment of the method of the invention is characterized in that the periodic wave has a ground frequency of between 15 and 35 MHz preferably between 20 and 30 MHz.

The preferred frequency range for carrying out the method of the invention, taking into account the performance of the ultrasound transducers and the sensitivity of the attenuation coefficient for residual stresses is between 15 and 35 MHz, with an optimum range extending between 20 and 30 MHz. For frequencies in this range, the sampling interval of the entry wave and of the exit wave is about 0.01 $\mu$sec. This is also the interval between successive points in the array defining the periodic wave.

One problem associated with measuring residual stresses using ultrasound measuring techniques is that the sensitivity of the attenuation coefficient for residual stresses occurs at ultrasound frequencies of above 50 MHz. At these frequencies, due to high attenuation it is difficult to obtain workable echo or exit signals from a wall of thick sections such as aluminium plates. The usable frequencies for aluminium plates is more or less limited to about 35 MHz at which the sensitivity of attenuation coefficient to variations in residual stresses is low. Lowering the frequency to 30 MHz yields less attenuation, although also the sensitivity for residual stress decreases. The challenge associated with using velocity measurements to monitor the variations of residual stress, is that the variations of residual stress in aluminium plates are typically in the order of 10 MP; this will cause velocity variations as small as 0.01 mm/$\mu$sec. For typical aluminium plates, this corresponds to a time-of-flight of about 50 nanoseconds. Presently available ultrasound instruments are typically incapable of measuring such small values of time specially in a production environment. Therefore, velocity measurement are not suitable for practical residual stress assessment and mapping.

The method of our invention makes it possible to use an ultrasound frequency that yields a workable echo or exit signal but at which frequency until now no practical time-of-flight variation due to residual stress variation would be measurable. Because the method of our invention is very sensitive to phase differences, and therefore time-of-flight variation, residual stress can be measured at these frequencies. The preferred range according to our method has an optimum in the sense of magnitude of echo or exit signal and time-of-flight variation due to residual stress.

For the avoidance of interference between the entry wave and a return wave, for ease of performing the calculations and presentation of the results and for simplicity of the construction of the equipment for carrying out the method, it is preferred that the entry ultrasound wave on which the calculation of the convolution integral is based is a burst of an ultrasound wave.

A further simplification of the equipment and the method is possible with an embodiment of the invention that is characterized by the selected entry gate time is equal to the selected exit gate time.

When the method is performed with a digital computer, only one gate time has to be defined, when the method is performed using electronic hardware gates, the number of different items can be reduced.

Surprisingly it has been found that the sensitivity and resolution of the method can be improved by a further embodiment of the invention that is characterized in that at least one of the electrical outputs of the detector for the entry wave and the exit wave is given a DC-offset prior to performing the convolution.

It also has been found that the length of the entry gate time, and in particular the length of the exit gate time also influences the sensitivity and resolution. The optimum value of both the DC-offset and the length of the selected gate time or gate times is dependent on the value of the ground frequency. The effect of mechanical or microstructural parameters on the attenuation and time-of-flight of an ultrasound wave is frequency dependent. Therefore, by selecting the correct frequency within a certain frequency range, the method according to the invention can be used for determining a chosen mechanical or microstructural parameter, such as grain size distribution, texture or residual stress. Also dependent on the parameter to be determined, the DC-offset and gate time, in particular the exit gate time, can be optimized.

It has shown that a very sensitive and high resolution measurement can be obtained when measuring residual stress with a method that is characterized in that at least one of the electrical outputs of the detector for the entry wave and the exit wave is given DC-offset prior to performing the integration of between 15 and 35% preferably between 20 and 30% of the maximum amplitude of the entry wave and the exit wave when measuring the residual stress. Preferably the DC-offset is a positive offset.

An embodiment of the method that is particularly beneficial to the user of the specimen is characterized in that the metal specimen is scanned by the ultrasound transducer and/or detector to form a plan view of the distribution of the residual stress.

To the user, the specimen in general is a semi-finished product from which he makes by machining the final product. A plan view, in particular a plan view showing areas with different residual stress, provides the user with the information he can take into account while machining so that the effect of residual stress on the final product is prevented or at least reduced to a large extent.

As explained before, the method according to the invention provides a very sensitive procedure for determining phase-angle, or in other words, the time-of-flight. Time-of-flight is however also affected by thickness. Time-of-flight variation due to thickness variation can in general be distinguished for time-of-flight variations caused by such parameter as residual stress. In case of a stretched aluminium plate, the variations of thickness, if any, progress smoothly across the plate whereas variations of time-of-flight due to residual stress are relatively abrupt. This difference can form a criteria for distinguishing one form from the other. A variety of procedures may be used to separate the time-of-flight indications of residual stress variations from those of thickness variations. One method, applicable in case the thickness varies smoothly across the plate, is based on the application of a moving average procedure. In case the thickness variation is less smooth across the plate and even may conceal residual stress variation, mathematical filter may be employed. Another possibility is to make a first high resolution, high accuracy scan to determine thickness variations across the plate and to make a subsequent scan to determine residual stress or another parameter and take into account the determination of the value of this parameter the thickness measured in the first scan.

A non-limitative example of performing the method is described below. According to the method, aluminium plates may be placed in a known manner in an immersion tank equipped with ultrasound scanning facilities i.e. a scanning bridge, transducer manipulator, and the necessary electronics including pulsers, receivers, preamplifiers, and a digital data acquisition and processing system. A broadband ultrasound transducer with frequency range of e.g. 15 to 25 MHz is used to acquire A-scan data. For each scanning increment, the entire A-scan is digitized. Using an entry gate and an exit gate, the entry surface (reference) and the first echo from the back wall of the plate are both captured.

Good results are obtained with a DC-offset of between 1–4 mV in a frequency range of the ground frequency between 20 and 30 MHz and at a gate time for both exit gate and entry gate of between 1 and 4 $\mu$seconds. The amplification is kept at such a level that the reference signal is clearly unsaturated. At this amplification, in order to obtain a workable back wall echo, a hardware time corrected gain (TCG) system is used to apply an amplification of 10 dB to 30 dB to the back wall signal only; this additional gain is taken into account in the attenuation calculations. The length of the gates which contain the reference and the back wall signals are set to a value which allows reasonable variations in time due to mechanical variations; this is in the order of 1.5 $\mu$seconds for each gate. The gate containing the reference signal is slaved to the reference signal by a, in time, "negative triggering" system; a peak detector is used to constantly detect the reference signal at the desired amplitude level, and by the "negative triggering" the gate is actually triggered before the signal begins to rise. The gate containing the back wall signal is slaved to the front surface gate. These two signals are then concatenated; this will enable the system to only process the two signals of interest and avoid the rest of the A-scan and thus reduce the processing time. Both signals are convoluted with a periodic sinusoid signal of the appropriate frequency and amplitude, i.e. for each signal, a sine and a cosine component is defined and the value of the convolution integral is calculated.

For each scan increment, the value of the convolution integral of the reference signal and of the back wall signal are calculated. For the reference signal the phase angle is constant as the position of this signal in the gate is slaved to the gate position. For the back wall signal, on the other hand, the phase angle of the component of ground frequency is not constant; it varies if the velocity of ultrasound in the plate charges due to microstructural variations such as caused by residual stresses in the plate. The arrival time of the back wall echo is directly related to variations in velocity. This variation corresponds to 50 nano seconds at frequencies which are used in this invention. For typical aluminium plates this corresponds to a velocity difference of 0.008 mm/$\mu$ second which has only a negligible effect when attenuation or velocity are measured. In the present invention, however, the typical variations of time-of-flight and the resulting phase shift will cause a variations of 0 to 0.5 cm$^{-1}$ in the "residual stress factor". In the C-scan obtained from. a plate, using the above mentioned method, the variations of "residual stress factor" can conveniently be displayed by a 128 level colour or black & white palette. The resulting C-scan clearly shows the distribution of the "residual stress factor" in the entire plate. In the final C-scan, values of residual stress in MP are shown by applying an equation which relates the values of residual stress to variations of the "residual stress factor". This relationship is established empirically by comparing values of "residual stress factor" with those obtained by destructive tests i.e. hole drilling or deflection tests performed on the samples taken from the respective areas of the plate. This relationship takes the form of a logarithmic relation that can be calibrated against values obtained by method describing before.

For measuring the residual stress factor, using a digital ultrasonic scanning system, the following procedure is used:

In order to simulate the front surface wave and the back surface wave forms in a periodic fashion, a sine array and a cosine array are defined with the following characteristics:

number of digitized points in each array sampling interval at which ultrasonic signal from the front surface wave and the back surface wave is digitized, e.g. 0.01 $\mu$sec.

frequency in MHz which corresponds to the center frequency of the front surface signal, e.g. 20 MHz.

In the next step of simulation, each front surface wave and back surface wave are processed by the previously defined sine and cosine arrays. The result is an array in the form of periodic wave for front surface and back surface wave forms. This is done as follows:

| (FS-Sine) | (Front Surface Sine wave array) | = Σ front surface wave × sine array |
| (FS-Cosine) | (Front Surface Cosine wave array) | = Σ front surface wave × cosine array |
| (BS-Sine) | (Back Surface Sine wave array) | = Σ back surface wave × sine array |
| (BS-Cosine) | (Back Surface Cosine wave array) | = Σ back surface wave × cosine array | wherein sommation takes place over the selected gate time.

Prior to the above process, preferably a DC-offset of between 2–3 mV is introduced to front and back surface waves. Following the process of simulation, a Fourier term is calculated for front and back surface using their corresponding sine and cosine array components:

Fourier Term of Front Surface=[(FS–Sine)$^2$+(FS–Cosine)$^2$]$^{1/2}$= AFS

Fourier Term of Back Surface=[(BS–Sine)$^2$+(BS–Cosine)$^2$]$^{1/2}$= BFS

The residual stress factor rsf is calculated from the Fourier terms:

rsf=[-Ln($^{AFS}/_{BFS}$)+T constant)]/distance wherein T constant is a term representing the incomplete transmission of sound at each boundary between different media.

The agreement between residual stress as measured, calculated and presented by the method according to the invention and calculations using the finite-element-method will be illustrated with reference to the drawing.

In the drawing, FIG. 1 shows the measured and calculated residual stress distribution across a rolled and stretched aluminium plate of 150 mm thickness and FIG. 2 shows the calculated residual stress of a part of the plate of FIG. 1 using a finite-element-method.

FIG. 1 shows the measured residual stress distribution and discloses across on aluminium plate of a thickness of 150 mm, a width of 1250 mm and a length of 5500 mm. The plate was rolled, heat treated and quenched and subsequently stretched prior to the residual stress measurement. The letters in FIG. 1 indicate, in increasing alphabetical order, areas with increasing residual stress. In the figure only larger areas are indicated and the range of residual stress is divided into only a limited number of steps.

FIG. 2 shows the residual stress as calculated with the finite-element-method for the right upper corner portion of the plate as limited by lines A, B of FIG. 1. Areas with comparable residual stress are indicated with the same letters.

In the finite-element calculations only planar effects due to rolling and stretching were taken into account, the effects of quenching were ignored. This accounts for the fact that the areas $c^1$ and $d_1$, of FIG. 2 do not extend parallel to the long side of the plate, but are confined areas. Taking this into consideration, the results of finite-element-calculation and of the residual stress measurement using the method of the invention show a very good agreement and confirm that this method is suitable for on-line, non-destructive residual stress measurement of large specimens.

FIGS. 3, 4, 5, 6 and 7 show examples of actual wave forms, processed data and a presentation of residual stress as measured with the method according to the invention.

FIG. 3 shows a representation of the entry, front surface, wave and of the exit, back surface, wave. The front surface wave and back surface wave are concatenated to reduce the processing time. Further it can be seen that both the front surface wave and the back surface wave have been offset by a DC-voltage.

The front surface wave and the back surface wave is sampled with a sample interval of 0.01 $\mu$sec. The sine and cosine array is defined with the same sample interval.

Figure 1:
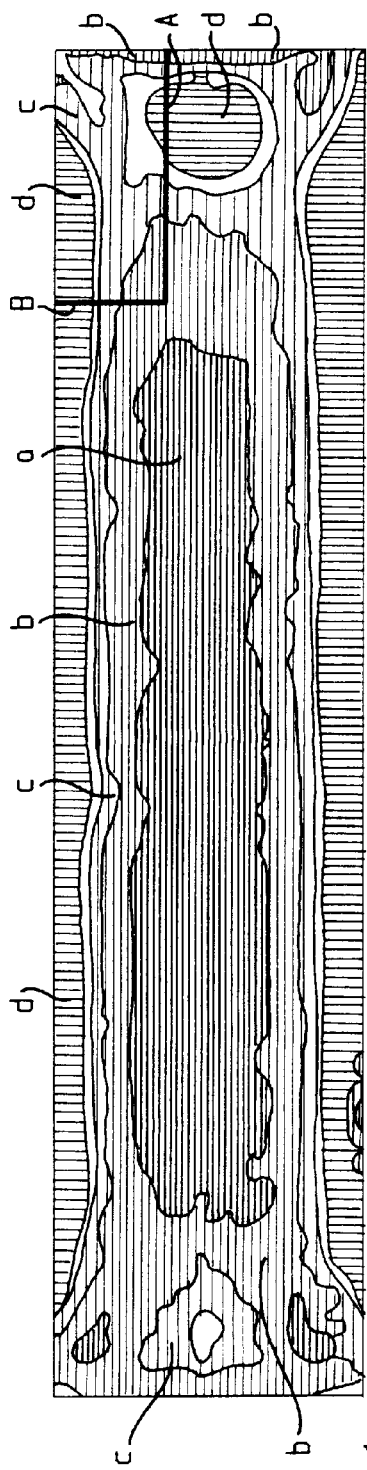
Figure 2:
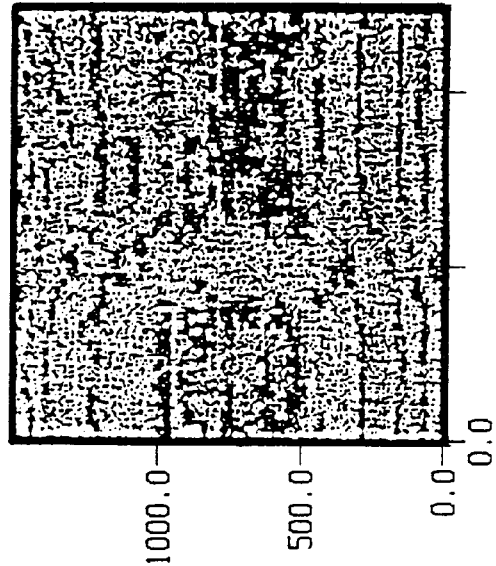
Figure 2:
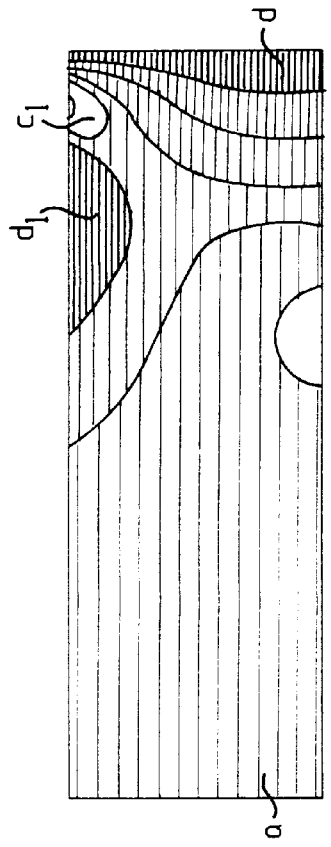
Figure 3:
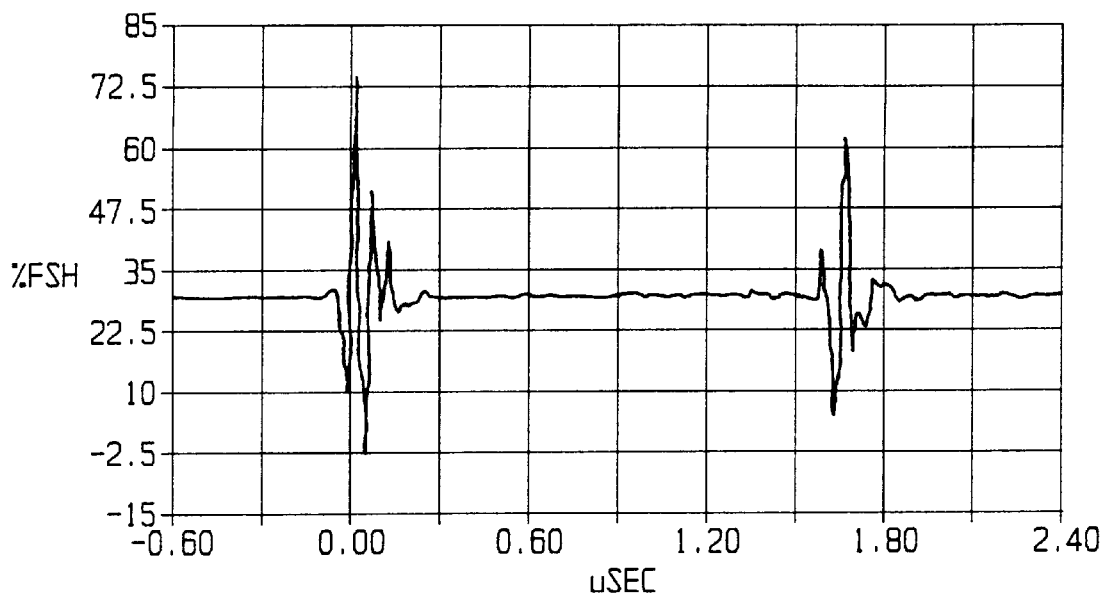
Figure 4:
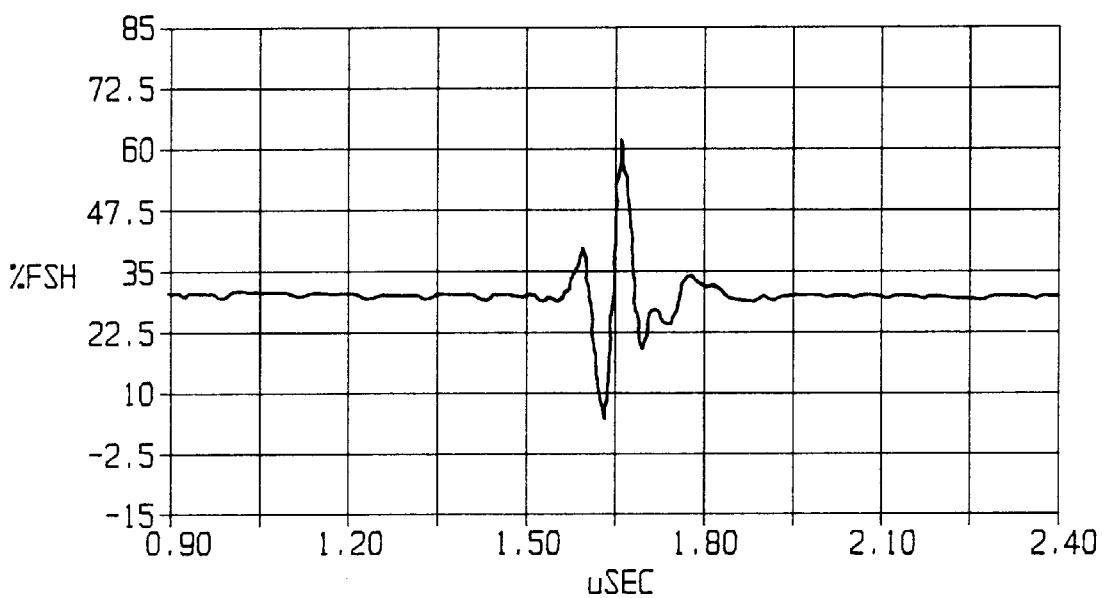
FIG. 4 shows on an extended time scale the front surface wave. It can be seen from FIG. 3 and FIG. 4 that negative triggering is used.
Figure 5:
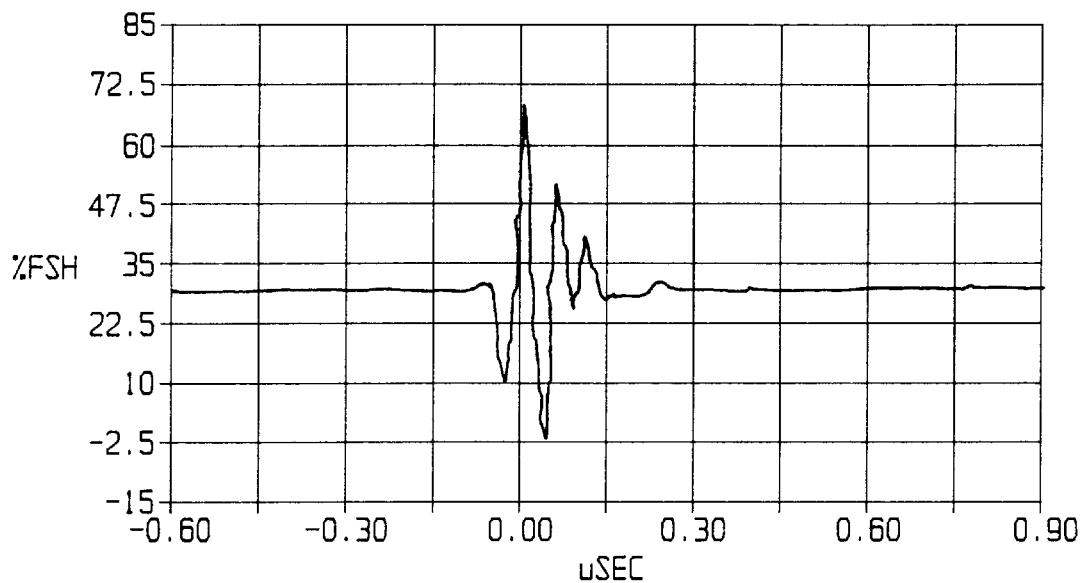
FIG. 5 shows on an extended time scale the back surface wave.

In FIGS. 3, 4 and 5 FSH stands for full scale height.

Figure 6:
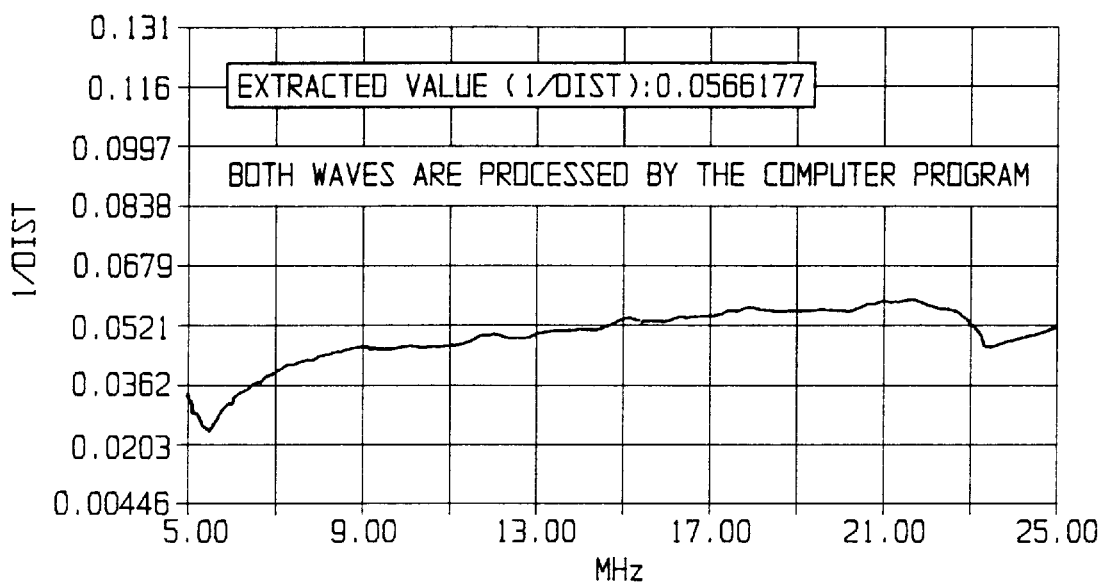

FIG. 6 shows the result of applying the method of the invention to the front surface wave and the back surface wave of FIG. 3 and 4 resp. performed over a wide frequency range. As can be seen from FIG. 6, the highest sensitivity in this case is obtained in the frequency range between 15 MHz and 23 MHz. The selected (extracted) value in the present example is 0.0566,77 per unit of length. The computer program performing the calculations is made such that it processes both front and back surface waves over a wide frequency range. This has the advantage that the program is applicable for ultrasonic transducers operating at different frequencies.

In order to obtain a C-scan, the plate under test is scanned. For each scan increment the front surface wave and the back surface wave are processed as described above and, if desired after feeding the result to one or more level comparators a C-scan of the residual stress can be made. Such C-scan showing the rsf distribution over the plate under test is shown in FIG. 7.

What is claimed is:

1. Method of measuring residual stress in a metallic specimen wherein, by means of an ultrasound transducer an ultrasound entry wave having a ground frequency $f_g$ is introduced into a surface of the metallic specimen, the amplitude of the ultrasound entry wave is measured by means of an entry wave detector and the amplitude of the succeeding ultrasound exit wave is measured by means of a exit wave detector and the measured values of the amplitude of the ultrasound entry and exit wave are used to determine residual stress, characterized in that, for a selected entry gate time $\tau_n$ the value of $$\int_o^{\tau_n} w_n(t) p_n(x-t)\,dt$$

wherein x is a constant, this integral also referred to as the entry convolution integral, of the measured ultrasound entry wave $w_n(t)$ and a periodic wave $p_n(t)$ of the ground frequency $f_g$ is calculated and during a selected exit gate time $\tau_x$ the value of $$\int_o^{\tau_x} w_x(t) q_x(y-t)\,dt$$

wherein y is a constant, this integral also referred to as the exit convolution integral, of the measured ultrasound exit wave $w_x(t)$ and a periodic wave $q_x(t)$ of the ground frequency $f_g$ is calculated and the residual stress is determined using the calculated values of the entry convolution integral and the exit convolution integral.

2. Method according to claim 1, wherein, the value of the convolution integral for both the entry wave and the exit wave is calculated for two symmetrical ¼ shifted periodic waves and the residual stress is calculated from the ratio of the square root of the sum of the squares of the calculated values of the exit convolution integrals and the entry convolution integrals respectively.

3. Method according to claim 1, wherein, the periodic wave $p_n(t)$ and $q_x(t)$ are sine-waves.

4. Method according to claim 1 for measuring the residual stress in a metallic specimen of aluminium, wherein, the periodic wave has a ground frequency of between 15 and 35 MHz preferably between 20 and 30 MHz.

5. Method according to claim 1, wherein, the selected entry gate time is equal to the selected exit gate time.

6. Method according to claim 1 wherein at least one of the detectors for the entry wave and the exit wave has an electrical output, wherein, at least one of the electrical outputs of the detector for the entry wave and the exit wave is given a DC-offset prior to performing the integration.

7. Method according to claim 6, wherein, at least one of the electrical outputs of the detector for the entry wave and the exit wave is given DC-offset prior to performing the integration of between 15 and 35% preferably between 20 and 30% of the maximum amplitude of the entry wave and the exit wave when measuring the residual stress.

8. Method according to claim 1, wherein, the metal specimen is scanned by the ultrasound transducer and/or detector to form a plan view of the distribution of the residual stress.

* * * * *